Figure 1:
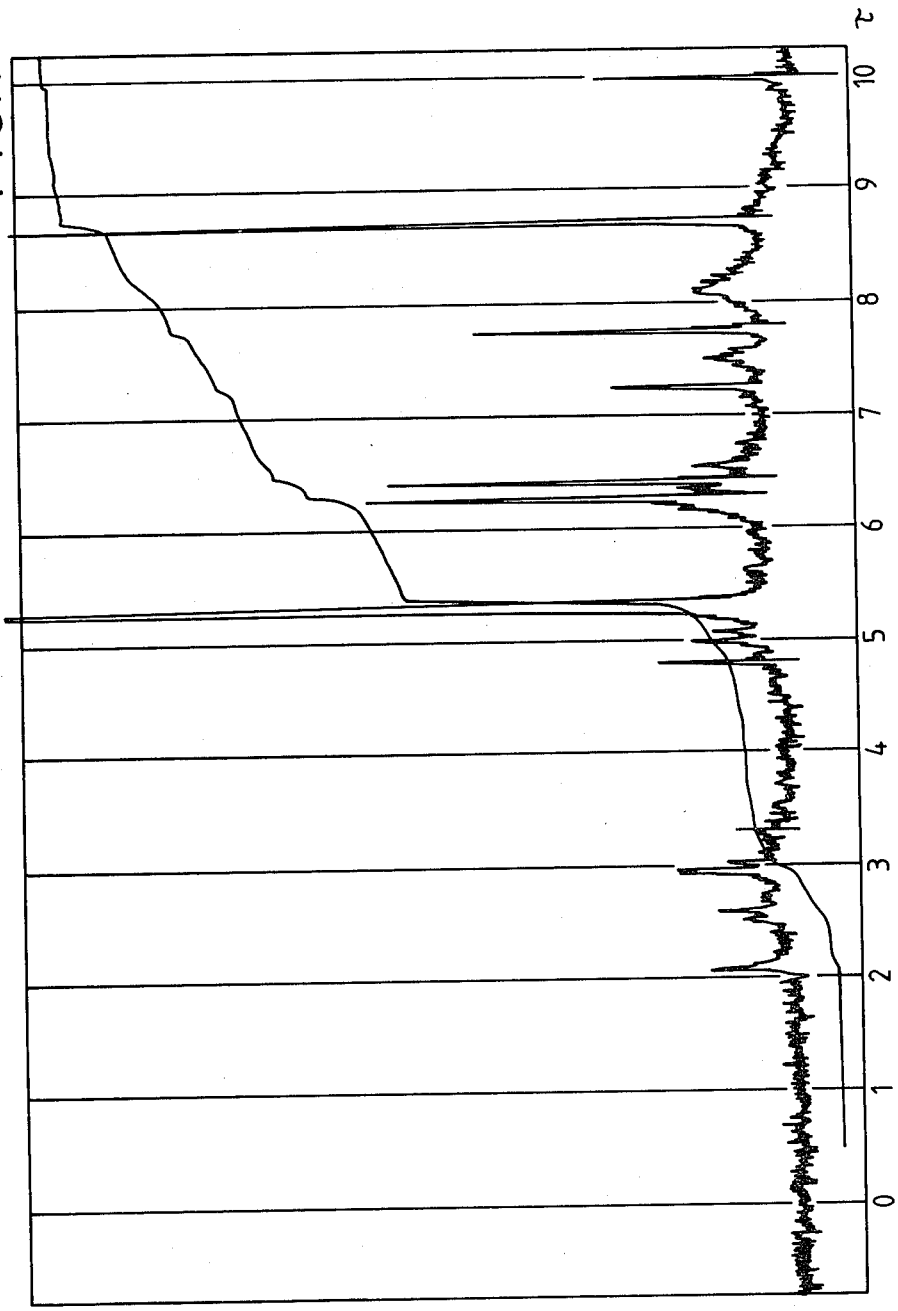

United States Patent [19]

Brown et al.

[11] 4,379,920

[45] Apr. 12, 1983

[54] CEPHALOSPORINS

[75] Inventors: David Brown, Hayes; Anthony F. Giles, Maidenhead; Howard W. Cramer, Berkhamsted; H. Mary Noble, Burnham; Louis J. Nisbet, Bourne End; Michael E. Bushell, Farnham; Glenis Weare, Tylers Green; Ian Y. Caldwell, Uxbridge, all of England

[73] Assignee: Glaxo Group Limited, England

[21] Appl. No.: 196,525

[22] Filed: Oct. 14, 1980

[30] Foreign Application Priority Data

Oct. 31, 1979 [GB] United Kingdom ............... 7937737
May 21, 1980 [GB] United Kingdom ............... 8016798

[51] Int. Cl.³ ............... C07D 501/57; A61K 31/545
[52] U.S. Cl. ............................ 542/427; 544/21; 424/246
[58] Field of Search ............ 542/427, 420, 421; 544/21; 424/246

[56] References Cited

U.S. PATENT DOCUMENTS 3,914,157 10/1975 Stapley et al. .
4,017,485 4/1977 Hasegawa et al. .
4,103,083 7/1978 Ogawa et al. ............... 544/21
4,259,326 3/1981 Gushima et al. ............ 542/427
4,302,578 11/1981 Stapley et al. ............. 542/427

Primary Examiner—Nicholas S. Rizzo

Attorney, Agent, or Firm—Bernard, Rothwell & Brown

[57] ABSTRACT

Cephamycin compounds of the formula (I)

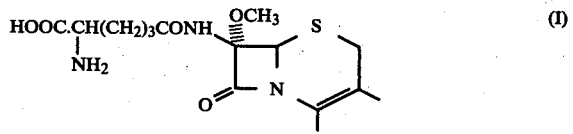

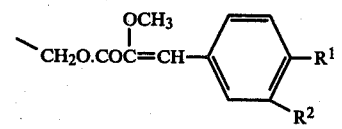

wherein $R^1$ represents hydroxyl or sulphooxy and $R^2$ represents sulphooxy together with derivatives thereof including salts, esters, N-protected derivatives and solvates thereof are disclosed. These compounds are of great value as intermediates in the preparation of other cephamycin compounds.

The compounds of the invention may be isolated from fermentation broths of strains of the genus Streptomyces which produce the compounds and a new such strain is described. The isolation of the compounds may be achieved by a liquid/liquid or liquid/solid ion-exchange technique, and is preferably achieved by the formation of an ion-pair in a liquid/liquid technique.

3 Claims, 6 Drawing Figures

CEPHALOSPORINS

This invention relates to improvements in or relating to cephalosporins. More particularly it relates to new cephamycin compounds which may be obtained by fermentation.

Fermentation of various strains of the genus Streptomyces has produced a number of β-lactam compounds possessing a wide range of antibiotic activity. British Patent Specification No. 1,321,412 for example describes 7α-methoxy-7β-(D-5-amino-5-carboxypentanamido)ceph-3-em-4-carboxylic acid compounds having a range of possible substituents in the 3-position amongst which are included α-methoxy-p-sulphooxycinnamoyloxymethyl and α-methoxy-p-hydroxycinnamoyloxymethyl groups. Such compounds are known as cephamycin A and cephamycin B respectively.

British Patent Specification No. 1,480,082 describes a further cephamycin called antibiotic C-2801-X. This is also produced by fermentation of a variety of strains of Streptomyces, including *Streptomyces heteromorphus* C-2801 (IFO 13575) and *Streptomyces panayensis* strains C-2878 (IFO 13576) and C-2879 (IFO 13577). Antibiotic C-2801-X is also a 7α-methoxy-7β-(D-5-amino-5-carboxypentanamido)ceph-3-em-4-carboxylic acid but has an α-methoxy-m,p-dihydroxycinnamoyloxymethyl group at the 3-position.

We have now found that fermentation of strains of the genus Streptomyces is capable of producing further cephamycin compounds not previously known, isolated or identified.

According to one aspect of the invention, we provide compounds of the formula (I)

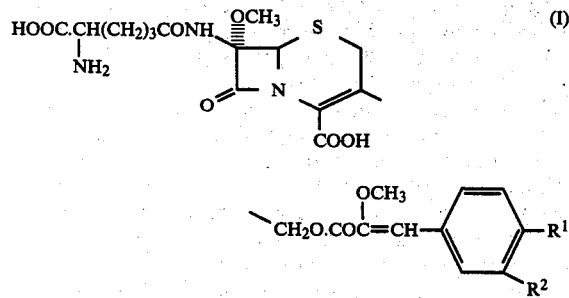

wherein $R^1$ represents a hydroxyl or sulphooxy (—O-SO$_3$H) group, and $R^2$ represents a sulphooxy group together with derivatives thereof. Suitable derivatives of the compounds of formula (I) will in general comprise salts, esters, N-protected derivatives, and solvates thereof.

The compounds of the invention have been found to possess some antibiotic activity against, for example, strains of *Haemophilus influenzae* and Proteus e.g. *Proteus vulgaris* and *Proteus mirabilis*. Moreover, the compounds of the invention have great value as intermediates in the preparation of other cephamycin compounds having antibiotic activity, for example for conversion into the corresponding 3-hydroxymethyl cephamycin whence other compounds having antibiotic activity may be made e.g. cefoxitin.

Such conversion may be effected enzymically using, for example, an esterase derived from a suitable source and constitutes another feature of the invention. Such a source includes a yeast source e.g. one or more strains of the species *Rhodosporidium toruloides* as described in British Patent Specification No. 1,531,212.

In addition, the compounds of the invention have been found easy to extract from fermentation broths.

Suitable salts of the compounds of the invention include the alkali metal, alkaline earth metal, ammonium and organic base salts, for example the sodium, potassium, lithium, calcium, magnesium, ammonium, trimethylammonium and triethylammonium salts. Salts may be formed either with the carboxylic acid functions, or the sulphonic acid functions or both. The invention further includes acid-addition salts formed on the amino group with, for example, mineral or other acids e.g. hydrochloric or tartaric acids.

According to a further aspect of the invention, we provide a process for the production of a compound of formula (I) as defined above which comprises cultivating a strain of the genus Streptomyces capable of producing a compound of formula (I) and isolating a compound of formula (I) or a derivative thereof from the culture medium, followed, if desired, by formation of the free acid or a derivative thereof.

Streptomyces strains capable of producing the compounds of formula (I) may be recognised by the following procedure.

A slope of the strain to be tested may be used to inoculate a growth medium such as Medium 2 described below. This culture may be allowed to grow for up to 3 days at 28° C. with agitation. The culture may then be used to inoculate (in a quantity of 3%) a fermentation medium such as Medium 3 described below. This fermentation stage is preferably carried out at about 22° C. for a period of 3 days with agitation. An aliquot of the final cultured broth, or concentrated cultured broth, may be applied to a t.l.c. (thin layer chromatography) plate along with, as standards, aliquots containing the compounds of the invention. After development in a solvent system (eg. acetonitrile:water, 7:3) the plates are overlaid with nutrient agar inoculated with *Proteus vulgaris* or *Comamonas terrigena* ATCC 8461 and an indicator (e.g. 2,3,5-triphenyl tetrazolium chloride). After incubation (e.g. at 37° C. for 18 hours) the zones of inhibition of the compounds of the invention applied as standards may be compared with any zones of inhibition of the broth under test. The presence of the compounds of the invention may then be confirmed by larger scale fermentation followed by extraction and characterisation as described herein.

The production of the compound of formula (I) by fermentation of a strain of the genus Streptomyces may be effected by conventional means, i.e. by culturing the strain in the presence of assimilable sources of carbon, nitrogen and mineral salts. Cultivation will preferably be carried out by submerged culture under aerobic conditions.

In the above-mentioned cultivation processes, the strain of the genus Streptomyces employed will preferably be a strain of *Streptomyces rochei*, for example strain NRRL 3973, or a high yielding mutant thereof, of a strain similar to *Streptomyces rochei*, given the number S3907C herein, deposited at the National Collection of Industrial Bacteria, Aberdeen, Scotland under No. NCIB 11533 on Aug. 31, 1979, or a high yielding mutant thereof.

Assimilable sources of carbon, nitrogen and minerals may be provided by either simple or complex nutrients. Sources of carbon will generally include glucose, maltose, starch, glycerol, molasses, dextrin, lactose, sucrose, carboxylic acids, alcohols, for example, methanol, n-paraffins and vegetable oils. Sources of carbon will generally comprise from 0.5 to 10% by weight of the fermentation medium.

Sources of nitrogen will generally include soyabean meal, corn steep liquors, distillers solubles, yeast extracts, cottonseed meal, peptones, ground nut meal, meat extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, phosphate, sulphate, chloride and carbonate ions.

An antifoam may be present to control excessive foaming and added at intervals as required.

Cultivation of the strain of the genus Streptomyces will generally be effected at a temperature of from 18°–37° C. preferably of from 20°–30° C., and will desirably take place with aeration and agitation e.g. by shaking or stirring. The growth medium may initially be inoculated with a small quantity of sporulated suspension of the microorganism but in order to avoid a growth lag a vegetative inoculum of the organism may be prepared by inoculating a small quantity of culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 5.5 to 7.5, and preferably at a pH of around 6.5.

In a preferred embodiment of the fermentation a slope of Streptomyces sp.S3907C may be used to inoculate a medium comprising sources of assimilable carbon e.g. glucose and/or glycerol, assimilable nitrogen, e.g. tryptones and/or complex mixtures of assimilable carbon and nitrogen, e.g. Pharmamedia, corn steep liquor, distiller's solubles and/or soya bean meal and/or yeast extracts, and nutrient minerals. This culture may be allowed to grow for up to 3 days at from 25°–35° C. with agitation.

The inoculum thus formed may then be used to inoculate (in a quantity of up to about 10%) a similar nutrient medium. Growth will desirably be carried out at from 20°–30° C. with agitation and aeration, in one or more stages, ending with a final fermentation stage which is normally effected in 2 to 10 days. In the final fermentation stage, it is preferred to use only low levels of phosphate ions.

The slope employed may be a conventional agar slope but it is preferred to use an agar slope containing lactic casein as the nitrogen source and soluble starch as the carbon source. Such a slope may be inoculated from an identical master slope seeded from a freeze-dried ampoule of the microorganism.

The compounds of the invention may be isolated from the fermentation by conventional isolation techniques. Thus, in general, the fermentation broth will be subjected to clarification by filtration, centrifugation and/or other techniques which will remove solid material and provide a solution containing the fermentation-derived compounds of the invention. It may also be possible to use the unclarified broth in certain adsorption-elution stages. The compounds may be isolated by a variety of fractionation and chromatographic techniques, for example adsorption-elution, precipitation, fractional crystallisation, solvent extraction, ion-pair extraction etc. which serve to remove other constituents of the fermentation broth. The presence of the sulphooxy groups renders the compounds of the invention readily extractable, particularly by methods involving ion-exchange, in view of their high acidity.

Thus, for example, the compounds of the invention may be separated from unwanted fermentation broth compounds by an ion-exchange extraction process. Such a process may involve either liquid/liquid or liquid/solid ion exchange techniques. If it is desired, this extraction may be preceded by one or more steps to clarify the fermentation broth and remove some unwanted impurities, for example by a filtration or centrifugation step and/or a washing step.

A suitable liquid/liquid form of extraction involves the formation of an ion-pair with a compound of the invention which partitions favourably into an organic solvent. Such ion-pair extraction may be carried out by extracting an aqueous medium containing the desired compound of the invention and/or a salt thereof with a solution of an amine or a salt thereof in a water-immiscible solvent (e.g. a hydrocarbon such as hexane or kerosene, a halogenated hydrocarbon such as dichloromethane, a ketone such as methylisobutylketone, or an alcohol such as n-butanol). The amine is preferably a compound the same as or similar to those described by Bailes, Hanson and Hughes; Chem. Eng. (1976) 83/18, p. 86 or by Flett D., Chem. and Ind. 1977, pp. 706–712. Such an amine may be a primary, secondary or tertiary alkylamine or a quaternary ammonium salt and may carry one or more long-chain aliphatic groups. Suitable reagents are, for example, benzyldimethyl-n-hexadecylammonium chloride or trioctylmethylammonium chloride. The pH of the system will depend upon the solvent and amine employed.

If desired, after separation of the phases, the compounds of the invention may then be back-extracted from the organic phase into an aqueous medium containing a suitable anion. Such an anion may be carbonate, hydroxide, sulphate, nitrate or halide preferably in combination with an alkali metal. A suitable aqueous solution contains, for example, potassium iodide.

Alternatively, the compounds of the invention may be extracted from the clarified or unclarified culture broth by a liquid/solid ion exchange technique, e.g. using a conventional solid anion exchange resin. Such a resin may carry either weakly or strongly basic amine groups. The resin may, for example, be a polystyrene, polyacrylic, epoxy-polyamine, phenolic-polyamine or cross-linked dextran resin and may be macroreticular or microreticular. The term 'resin' is used herein for convenience also to include cellulosic derivatives and the above dextran derivatives which are derived from naturally-occurring polymers. Typical resins which may be used include Amberlite IRA 93 (styrene-divinylbenzene, weakly basic, macroreticular), Amberlite IRA 68 (acrylic-divinylbenzene, weakly basic, microreticular), Amberlite IRA 400 (styrene-divinylbenzene, strongly basic, microreticular) and Amberlite IRA 900 (styrene-divinylbenzene, strongly basic, macroreticular).

Such ion exchange resins are advantageously in salt form when contacted with the solution containing the compounds of the invention. The anion is conveniently the chloride ion, but different anions may be used without significant adverse effects. Because of their high acidity, the compounds of the invention are preferentially absorbed over the more weakly acidic impurities of the fermentation broth.

It is preferred to use a solution of an alkali metal chloride to elute compounds of the invention from the anion-exchanger, conveniently sodium chloride.

Compounds more weakly acidic than compounds of the invention will generally be eluted before the compounds of the invention. It may be advantageous to elute the ion-exchange resin with increasing concentrations of eluant in a suitable solvent and/or to fractionate the eluate.

If any steps are taken to assist in removal of undesired impurities before the use of ion-exchange techniques, these will desirably include a centrifugation and/or filtration step to remove coarse matter from the culture broth. A washing step may be carried out after filtration and/or centrifugation if desired in order to further reduce the level of unwanted impurities in the culture broth prior to ion-pair or other form of extraction of the compounds of the invention. Such washing may be effected using an organic solvent e.g. an ester such as ethyl acetate, an alcohol such as n-butanol or a ketone such as methylisobutylketone.

Once the compounds of the invention have been extracted from the culture broth, a variety of techniques may be employed in order to separate further and isolate the compounds of the invention.

Thus, for example, the compounds of the invention extracted from fermentation broth may be applied to one or more materials which may retain either the desired compounds or the undesired contaminants. Prior to such application, the aqueous solution may be concentrated e.g. by evaporation.

Thus, for example, the aqueous solution may be treated with an adsorbent carbon on which the fermentation derived compounds of the invention are adsorbed. This assists in separating further unwanted components, particularly unwanted salts, from the desired compounds. In general, the aqueous solution may be passed through a carbon bed, e.g. in a column, preferably using just sufficient carbon to adsorb all the desired compound usually in a ratio of about 1 part by volume of carbon to 3-10 parts by volume of solution.

The desired substances may then be eluted from the carbon with an aqueous water-miscible organic solvent, e.g. an alcohol, such as methanol or ethanol or isopropanol, or a ketone such as methyl ethyl ketone, methyl isobutyl ketone or, preferably, acetone, advantageously at a concentration of from 30% to 95%, preferably 50 to 70%. Before elution, the carbon is preferably washed e.g. with water, to remove non-adsorbed solution constituents.

Alternatively, the aqueous solution containing the compounds of the invention may be applied to a non-ionic resin e.g. the polystyrene resin XAD-2 (Surface Area 330 $m^2/gm$; Average Pore Diameter 90 Å; Porosity 0.40-0.45) or XAD-4 (Surface Area 7.25 $m^2/gm$; Av. Pore Diameter 40 Å; Porosity 0.45) or carbonaceous adsorbent Ambersorb XE-348, all available from Rohm & Haas (UK) Ltd., which retain the compounds of the invention but which do not retain several other significant solution components, e.g. salts. Elution may be effected using any of the aqueous water-miscible organic solvents detailed above.

Where the compounds of the invention occur together and are both present in aqueous solution following one or more of the separation and purification steps described above, separation of the compounds of the invention from each other and from structurally related compounds will generally be achieved by chromatography, for example anion-exchange chromatography. The anion-exchange resin will desirably be any of those described above. Typical basic resins which may be used also include the quaternary ammonium exchanger QAE-Sephadex (sold by Pharmacia U.K. Ltd.) or Dowex-1 (sold by Bio-Rad Laboratories Limited). Such ion exchange resins are advantageously in salt form when contacted with the solution containing the compounds of the invention. The anion is conveniently the chloride ion, but different anions may be used without significant adverse effects.

It is preferred to use a solution of an alkali metal salt to elute the compounds of the invention from the anion-exchanger. The salt is conveniently sodium chloride. In order to separate the compounds of the invention from each other and from structurally related compounds, it may be desirable to use a salt gradient.

Further purification and/or isolation of the compounds of the invention may be effected by further chromatography e,g, on silica or more preferably on an organic solvent-compatible, cross-linked dextran such as Sephadex LH 20 (sold by Pharmacia U.K. Ltd.) which contains the hydroxypropyl residues. The solution of the compound(s) obtained from previous stages may be too dilute for application to the column and may conveniently be concentrated by evaporation under reduced pressure. The column carrying the desired compound may be eluted, for example using a solvent of suitable polarity, e.g. aqueous acetonitrile.

Finally, fractions containing the desired compound(s) may be combined and evaporated to yield the desired compound(s).

By a suitable combination of the foregoing procedures, the compounds of the invention have been isolated.

There are now described some particularly useful sequences or variations of purification steps of the type described above.

Thus, fermentation broth is optionally acidified to about pH 4.0 and the broth is sieved in order to remove coarse solid material. The broth may then be clarified e.g. by centrifugation and the clarified broth extracted with an organic solvent, e.g. n-butanol and the organic extract discarded. The aqueous broth remaining may then be concentrated e.g. by evaporation which assists in removing further traces of organic solvent. The concentrate may then have its pH adjusted e.g. with a base to around neutrality e.g. 6.5 to 7.4 prior to ion-pair extraction.

Ion-pair extraction may be carried out using a quaternary ammonium salt, for example a benzyl dimethyl hexadecyl ammonium halide at about 0.2% w/v in an organic solvent, e.g. a halogenated hydrocarbon such as dichloromethane. The phases may be agitated together and then separated by centrifugation. The organic solvent extracts may be combined and the activity back extracted using an aqueous salt solution, for example potassium iodide. The extracts may be bulked and concentrated and desalted by adsorption on a non-ionic resin e.g. XAD-4, followed by washing the column with water and eluting into fractions with an aqueous organic solvent e.g. an alcohol or ketone such as methanol or acetone. After bulking, concentrating and freeze-drying the active fractions, e.g. those showing antibacterial activity against *Proteus vulgaris* and *Comamonas terrigena* ATCC 8461, the bulked solution may be examined for principal acid components by h.p.l.c. and their column capacity ratios noted to enable identification. To separate these components, an aqueous solution of the mixture may be applied to a strong anion exchange resin e.g. QAE-Sephadex in a chloride cycle. The column may be eluted with an alkali metal chloride gradient. Various groups of fractions may contain activity and may be individually bulked. One group may contain the compound of the invention in which $R^1$ represents a hydroxy and $R^2$ represents a sulphoxy group. Another group may contain a compound in which both $R^1$ and $R^2$ represent sulphooxy and another group may contain cephamycin A.

The individual fractions may be further purified e.g. by desalting on XAD-4, and eluting with an aqueous organic solvent e.g. acetone or methanol. The fractions obtained may be bulked and freeze-dried to yield the individual compounds.

In an alternative procedure, the fermentation broth may simply be filtered, using a filter aid if desired, before ion-pair extraction. A similar procedure to that outlined above may then be followed.

The strain *Streptomyces rochei* NRRL 3973 which may be used in the process of the present invention is a known strain and is described on pages 27 and 28 of British Patent Specification No. 1,321,412 under number MA-2938. Further morphology, and comparative morphology of another strain, *Streptomyces* sp. S3907C employed in the process of the present invention are given below:

Streptomyces sp. S3907C and *S. rochei* (NRRL 3973) Origin

S3907C was isolated from a Belgian soil sample which was air dried and suspended in sterile distilled water. Dilutions of the supernatant were plated onto starch-casein agar and incubated at 28° C. for 10-14 days.

*S. rochei* NRRL 3973 was obtained as a freeze-dried ampoule from the Northern Regional Research Laboratories culture collection.

DESCRIPTION OF THE ORGANISMS

On the preferred sporulation medium, medium 4 described below (starch casein agar), S3907C grows abundantly and produces aerial mycelium bearing spores in chains forming large hooks and loops. The sporophore has a grey colour and the reverse pigment is grey-brown. On the same medium *S. rochei* NRRL 3973 produces fewer spores in chains of short tight spirals of 3-5 turns. The *S. rochei* NRRL 3973 sporophore is white and the colony has cream reverse pigmentation.

The spores of both organisms are smooth walled and ellipsoidal to cylindrical in shape.

S3907C and *S. rochei* NRRL 3973 were grown on a variety of agar media including some recommended by the International Streptomycete Project (Shirling et al. (1968). Inst. J. Syst. Bacteriology, 18, 69-189). The cultures were grown at 28° C. for 14 days and then scored for substrate mycelium, aerial mycelium, spore colour and reverse pigment. Of the 20 media used, S3907C was similar to *S. rochei* NRRL 3973 on media 1-7 but the two cultures showed differences in the recorded characteristics on media 8-20 (Table 1).

Carbohydrate utilisation by S3907C and *S. rochei* NRRL 3973

Both cultures grew on 10 of the eleven carbon sources and failed to grow on cellulose. However, S3907C sporulated on the 10 media whereas *S. rochei* NRRL 3973 produced spores only on galactose and inositol as carbon sources (Table 2).

TABLE 1

Distinguishing features of S3907C and *S.rochei* NRRL 3973 on 20 agar media

| Agar Medium | Growth* S3907C | Growth* S. rochei NRRL 3973 | Spore colour S3907C | Spore colour S. rochei NRRL 3973 | Reverse pigmentation S3907C | Reverse pigmentation S. rochei NRRL 3973 |
|---|---|---|---|---|---|---|
| Nutrient | + | + | — | — | — | — |
| Glucose peptone | ++ | ++ | white | white | yellow | rust |
| Czapek Dox I | ++ | ++ | white | white | cream | yellow |
| Glycerol | ++ | ++ | — | — | yellow | yellow |
| Cytophaga | + | + | — | — | cream | cream |
| Cattleya No. 1 | ++ | ++ | — | — | cream | cream |
| Sporulation agar | ++ | + | — | — | cream | off-white |
| Glucose nutrient | ++ | ++ | white | — | cream | cream |
| Potato dextrose | +++ | +++ | grey | grey/brown | yellow | rust |
| Starch casein + actidione (50 μg/ml) | +++ | ++ | grey | grey/brown | yellow | yellow |
| Minimal + glucose + PYE | + | + | grey | — | cream | cream |
| Yellow agar | ++ | + | white | — | cream | cream |
| Oatmeal | +++ | +++ | grey | grey | cream | rust |
| Malt yeast | +++ | ++ | grey | grey/brown | brown | dark yellow |
| Yeast cerulose | ++ | + | grey | — | off-white | off-white |
| Malt | ++ | + | white | white | cream | dark yellow |
| Saboroud Malt | ++ | +++ | white | white | amber | dark orange |
| MYPG | +++ | ++ | white | white | off-white | off-white |
| Minimal glucose | + | + | grey | white | off-white | off-white |
| Starch casein | +++ | ++ | grey | white | grey/brown | cream |

*Growth
+ = very poor growth
++ = substrate mycelium; poor or no sporulation
+++ = abundant substrate and aerial mycelium

TABLE 2

Carbohydrate utilisation by S3907C and *S.rochei* NRRL 3973

| Carbon source | S3907C growth | S3907C sporulation | S.rochei NRRL 3973 growth | S.rochei NRRL 3973 sporulation |
|---|---|---|---|---|
| glucose | + | + | + | — |
| arabinose | + | + | + | — |
| fructose | + | + | + | — |
| galactose | + | + | + | + |
| inositol | + | + | + | + |
| mannitol | + | + | + | — |
| raffinose | + | + | + | — |
| rhamnose | + | + | + | — |
| sucrose | + | + | + | — |
| xylose | + | + | + | — |
| cellulose | — | — | — | — |

TABLE 2-continued

| Carbohydrate utilisation by S3907C and S.rochei NRRL 3973 | | | | |
|---|---|---|---|---|
| | S3907C | | S.rochei NRRL 3973 | |
| Carbon source | growth | sporu- lation | growth | sporu- lation |
| Medium 9* | — | — | — | — |

*Medium 9 is the carbon utilisation medium of Shirling, E. B. and Gottlieb, D. M. (1966). International J. Syst. Bact. 16(3), 313-340.

Cultures were grown on Medium 9 alone, or supplemented with the various carbon sources indicated in the Table and incubated at 28° C. for 25 days.

The invention will now be more particularly described in the following non-limiting Examples.

In the following Examples, all temperatures are in °C.

H.p.l.c. is high performance liquid chromatography and was carried out as follows: samples were chromatographed on a column (100 mm×5 mm diam.) of Partisil 10 SAX (10µ particle size). The factors were eluted at 1500 p.s.i. with water containing a gradient of $KH_2PO_4$ which increased from 5 g/liter to 50 g/liter in 3 min and then remained constant at 50 g/liter for a further 3 min. The flow rate of the eluant was 5 ml/min. The factors were detected by their absorption at 280 nm.

The Column Capacity Ratio is calculated as the difference between the retention times of the retained peak and the unretained peak divided by the retention time of the unretained peak.

Media used in the fermentation of Streptomyces sp. S3907C were as follows:

| Medium 1 | |
|---|---|
| Malt extract (Oxoid) | 24 g |
| Yeast extract (Difco) | 5 g |
| Agar (Oxoid No. 3) | 15 g |
| Tap water | 1 liter | pH adjusted to 7.8 with 40% (w/v) potassium hydroxide solution.

| Medium 2 | |
|---|---|
| Protein extract obtained from cotton seed (Pharmamedia) | 20 g |
| Glycerol | 10 g |
| Glucose | 5 g |
| Tap water | 1 liter |

| Medium 3 | |
|---|---|
| Glucose (Cerelose) | 25 g |
| Corn steep liquor | 15 g |
| Distillers solubles (Scotaferm) | 10 g |
| Protein extract (Pharmamedia) | 5 g |
| $CoCl_2.6H_2O$ | 0.01 g |
| Tap water | 950 ml | pH adjusted to pH 7.3 and sterilised, then calcium carbonate (3 g), suspended in tap water (50 ml) and sterilised, was added.

| Medium 4 | |
|---|---|
| Lactic casein | 1 g |
| Sodium hydroxide (N) | 2 ml |
| $KH_2PO_4$ | 2.1 g |
| Soluble starch (Analar) | 10 g |

| Medium 4 | |
|---|---|
| Agar (Oxoid No. 3) | 12 g |
| Distilled water | 1 liter |

| Medium 5 | |
|---|---|
| Bibbys milled Soya Bean Meal | 10 g |
| Dextrose Monohydrate | 20 g |
| Calcium Carbonate | 0.2 g |
| Cobalt Chloride.$6H_2O$ | 0.001 g |
| Sodium Sulphate anhydrous | 1 g |
| Tap water | 1 liter |

All media were sterilised for 30 to 120 minutes at 120° C. and 15 p.s.i.

Pharmamedia may be obtained from Traders Oil Mill Company, Fort Worth, Tex., U.S.A.

Cerelose may be obtained from C.P.C. (United Kingdom) Ltd., Trafford Park, Manchester.

Scotaferm may be obtained from Thos. Borthwick (Glasgow) Ltd.

Cellulose powder BEOO from Rettenmaier and Sohne was obtained through A. A. Reid, 15 Meadowbank Crescent, Edinburgh.

Dicalite was obtained from Steetley Chemicals Ltd., Abbey Mills, Canning Road, Stratford, London E.15.

In the Examples, the novel active constituents isolated are identified by factor numbers. S3907C/3 is the compound of the invention in which both $R^1$ and $R^2$ represent sulphooxy groups.

S3907C/4B is the compound of the invention in which $R^1$ is hydroxyl and $R^2$ a sulphooxy group.

EXAMPLE 1

(a) Streptomyces sp. S3907C was seeded directly from a freeze-dried ampoule onto an agar slope prepared from Medium 1. A dry scraping from this master slope was then used to inoculate further slopes of Medium 1 which were grown at 28° for 14 days.

Sterile water (10 ml) was added to each slope and the spores scraped off the surface with a pipette. From the resulting suspensions, portions (2.5 ml) were transferred to flasks containing Medium 2 (150 ml). The flasks were incubated for 48 hours at 28° on a rotary shaker.

Each flask was then used to provide an inoculum (130 ml) for a 5 liter fermenter, containing Medium 2 (4 liters). Silicone emulsion 525 antifoam (Dow Corning Limited, Barry, Glamorgan) was added (0.05% v/v) to prevent foaming; further additions were made as necessary. The broth was stirred for 48 hours at 28° with air supplied at a rate of 4 liters/min.

After microscopic and mycelial volume analysis, the best grown vessels were used to supply 15 liters of inoculum to the fermentation stage vessel containing approx. 450 liters of Medium 3. The broth was stirred at a constant temperature of 22° and air was supplied at a rate of 425 liters/min. Silicone emulsion 525 antifoam was added at batching (0.05% v/v) and further additions made when necessary during the fermentation. The broth was harvested after 140 h.

(b) The harvest broth (330 liters) was adjusted to pH 4 with sulphuric acid (1700 ml) and coarse solids were removed from the broth by sieving. The broth was then clarified by centrifugation. The supernatant fluid (244 liters, pH 4.4) was extracted with 2×½ volume n- butanol (122 liters) by stirring for 20 mins and then separating the phases on a centrifuge. The two butanol extracts were discarded. The aqueous phase (205 liters, pH 4.35) was transferred to a pot still and evaporated to remove traces of butanol. The pH of the concentrate (106 liters, pH 4.2) was adjusted to 6.8 with 40% sodium hydroxide solution (113 ml). This was then extracted with 3×⅓ volume dichloromethane (56 liters) containing 0.2% benzyl dimethyl-n-hexadecyl ammonium chloride by stirring for 20 mins and then separating the phases by centrifugation.

The dichloromethane extracts were bulked (158 liters) and the activity back extracted with 3.5% potassium iodide solution (1/50 followed by 1/100 volume). The mix was stirred for 15 mins and then phases separated under gravity. The two potassium iodide extracts were bulked (4.54 liters) and excess solvent removed by rotary evaporation at 30°.

To the concentrated back extract (1.5 liters) was added 5% (w/v) NaCl then the solution was passed down a column (200 ml bed vol.) of XAD-4. The column was washed with water (200 ml) and eluted with 60% (v/v) aqueous acetone; the eluate was collected in 50 ml fractions. Fractions 2-4, showing antibacterial activity against *Proteus vulgaris* and *Comamonas terrigena* ATCC 8461, were combined, concentrated by rotary evaporation and freeze-dried to give 1.25 g solid. The solid was shown by h.p.l.c. to contain three strongly acidic components with u.v. absorption at 280 nm and column capacity ratios 6.2, 8.6 and 14.6 respectively.

The solid (1 g) was dissolved in 5 ml water and applied to a column (200 ml bed vol.) of QAE Sephadex in the Cl-cycle. Elution was with a 0 to 5% (w/v) linear gradient of aqueous lithium chloride (1,000 ml) followed by 5% lithium chloride (500 ml) then 10% lithium chloride (500 ml). Eluate was collected as fractions of 25 ml which were examined by h.p.l.c. and by bioassay against *Proteus vulgaris*.

Three groups of fractions (Nos. 41-43, 47-51 and 68-73) were shown to have antibacterial activity. Each group was bulked separately and chromatographed on a column (20 ml) of Ambersorb XE-348. In each case the bioactivity was eluted with 60% aqueous acetone and freeze-dried to yield respectively 18.6 mg, 13.3 mg and 25.3 mg of solid.

The solid from fractions 41 to 43 was shown by h.p.l.c. to contain cephamycin A[7β-(D-5-amino-5-carboxy pentanamido)-7α-methoxy-3-(α-methoxy-p-sulphooxy cinnamoyloxymethyl)ceph-3-em-4-carboxylic acid], as the lithium salt. This compound had a column capacity ratio of 6.2.

The solid from fractions 47 to 51 was shown by h.p.l.c. to contain factor S3907C/4B, as the lithium salt, and had a column capacity ratio of 8.6.

The solid from fractions 68 to 73 was shown by h.p.l.c. to contain factor S3907C/3, as the lithium salt, and had a column capacity ratio of 14.6.

EXAMPLE 2

Streptomyces sp. S3907C was fermented in a manner similar to that of Example 1(a).

Harvest broth (440 liters, pH 7.9) was filtered on a rotary drum filter using Rettenmaier cellulose (3 kg) for the bed and adding Dicalite 478 (7.5 kg) as filter aid.

The pH of the filtrate (340 liters, pH 7.9) was adjusted to pH 4 with sulphuric acid (220 ml).

A portion of the filtrate (300 liters) was extracted with 2×½ volume n-butanol (150 liters) by stirring for 20 mins and then separating the phases on a centrifuge. The butanol extracts were discarded. The aqueous residue (260 liters, pH 4.1) was concentrated on a pot-still to remove traces of solvent and the pH adjusted from 4.1 to pH 6.8 with 40% w/v sodium hydroxide solution (102 ml).

This solution (228 liters) was extracted with 3×⅓ volume dichloromethane (76 liters) containing 0.2% benzyl dimethyl n-hexadecyl ammonium chloride by stirring for 20 mins and then separating the phases on a centrifuge. The dichloromethane extracts were bulked (228 liters) and the activity back extracted with 3.5% potassium iodide solution (1/50 volume followed by 1/100 volume). The mix was stirred well for 15 mins and then phases separated under gravity. The two potassium iodide extracts were bulked and concentrated to remove traces of solvent.

The concentrated extract (5.74 liters) was passed down a column (1.5 liters) of XAD-4, which was then washed with water (1.5 liters) and eluted with 60% aqueous acetone, the eluate being collected as fractions of 500 ml. Fractions 2 and 3 with strong antibacterial activity against *Proteus vulgaris* were combined, concentrated and freeze-dried to give 18.25 g solid.

The solid (10 g) was dissolved in the minimum volume of water and applied to a column (460 ml bed vol.) of QAE Sephadex Cl- cycle). This was eluted with a 0-10% (w/v) linear gradient of lithium chloride (total 2.0 liters) then with 10% (w/v) lithium chloride. Eluate was collected as 5 fractions of 50 ml then 135 fractions of 25 ml. Fractions were examined by bioassay against *Proteus vulgaris* and by h.p.l.c.

H.p.l.c. showed fractions 51 to 55 to contain cephamycin A and fractions 59 to 66 to contain factor S3907C/4B. These two groups of fractions were each applied to a column of XAD-4 which was eluted with 60% aqueous acetone. The eluate was concentrated and freeze-dried to yield a solid. The solid from fractions 51 to 55 (122 mg) contained cephamycin A as the lithium salt; h.p.l.c. showed a column capacity ratio identical to an authentic sample of cephamycin A. The solid from fractions 59 to 66 (241 mg) contained factor S3907C/4B as the lithium salt and had the following properties:

| U.v. | λmax | E: |
|---|---|---|
| | 290 | 233 in phosphate buffer, pH7 |
| | 292 | 230 in neutral or acidic MeOH |
| | 353 | in alkaline MeOH (10 mmolar NaOH) |
| N.m.r. | | Compatible with structure of factor S3907C/4B |
| I.r. | | Bands at 1766 cm$^{-1}$ (β-lactam) |
| | | 1700 cm$^{-1}$ (CO$_2$R) |
| | | 1276 cm$^{-1}$ (OSO$_3$Li) |
| | | 1245 cm$^{-1}$ (OSO$_3$Li) |

Figure 2:
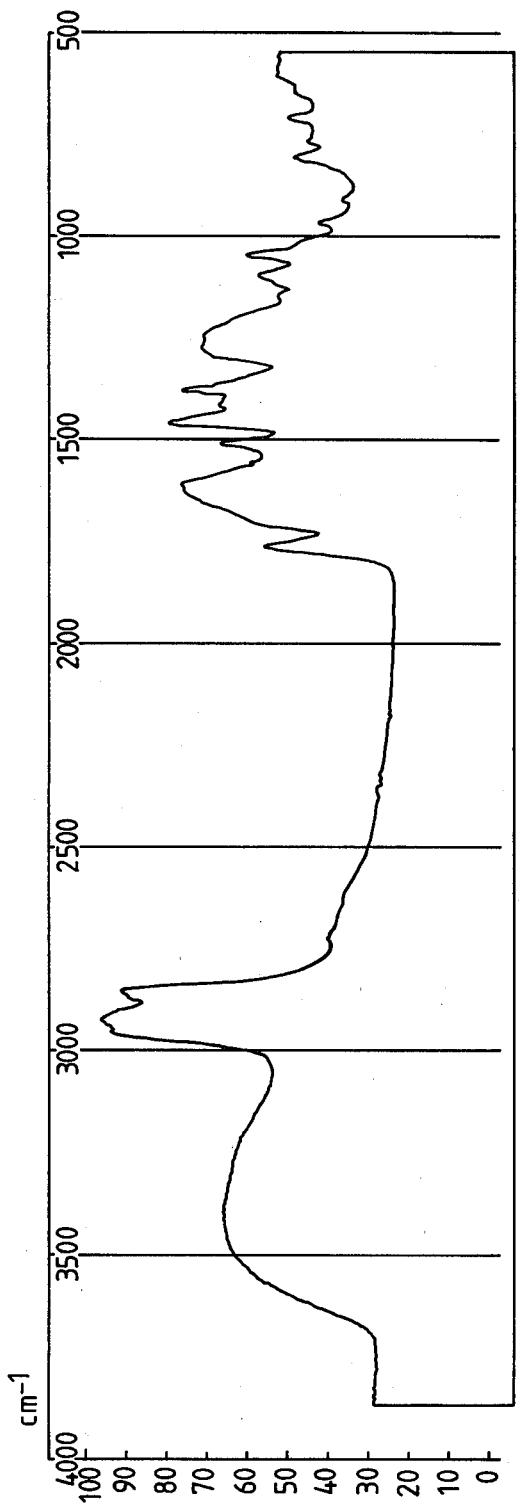

The N.m.r. and I.r. spectra are shown in FIG. 1 and FIG. 2 respectively.

EXAMPLE 3

Streptomyces sp. S3907C was fermented according to the method of Example 1(a), except that Medium 4 was used for the agar slopes, the calcium carbonate was omitted from Medium 3 and the final fermentation was controlled at pH 6.5 with additions of hydrochloric acid and sodium hydroxide. Broth was harvested after 92 hours.

Harvest broth (470 liters, pH 6.7) was filtered on rotary filter using a Rettenmaier cellulose bed (8 kg) and adding Dicalite 478 as filter aid (7.5 kg).

The filtrate (390 liters, pH 7.1) was extracted with $2 \times \frac{1}{3}$ volume of dichloromethane containing 0.2% benzyl dimethyl-n-hexadecyl ammonium chloride by the method of Example 2. The extracts were back extracted into a potassium iodide solution and the back-extracts treated with XAD-4 in a method similar to that of Example 2, the column being eluted with 60% aqueous methanol and the eluate being collected as fractions of 500 ml. Fractions were examined by h.p.l.c. and by bioassay against *Proteus vulgaris*. Those fractions which were shown by h.p.l.c. to contain factor S3907C/3 were combined, concentrated and freeze-dried to give 25.7 g solid.

The solid (20 g) was dissolved in 12% (w/v) aqueous NaCl (50 ml) and the solution applied to a column (500 ml bed vol.) of QAE Sephadex in the $Cl^-$ cycle. The column was eluted with 12% (w/v) NaCl, collecting fractions of 25 ml. On the basis of hplc examination fractions 46-64, containing factor S3907C/3, were combined and desalted by absorption on a column of XAD-4 (200 ml) and elution with 60% aqueous methanol. The active eluates were concentrated and freeze-dried to yield 603 mg crude factor S3907C/3 ($E_1^1$ 172 at $\lambda$max 288 nm in MeOH).

The crude solid (500 mg) was further purified by chromatography on a column of Sephadex LH20 (5 cm $\times$ 61 cm; 1200 ml bed vol.) packed in acetonitrile-water (7:3). The column was eluted with the same solvent, fractions of 25 ml being collected and assayed by h.p.l.c. and by bioassay against *Proteus vulgaris*. Fractions 48-52 were combined and concentrated to an oil by rotary evaporation.

The oil was dissolved in 2.5 ml of 3% (v/v) aqueous methanol and applied to a column (200 ml bed vol.) of XAD-4 packed in this solvent. The column was eluted with 3% methanol, fractions of 25 ml being collected. Fractions 3-12 were combined, concentrated by rotary evaporation and freeze-dried to give 64 mg solid.

The solid (64 mg) was dissolved in 0.6 ml water and the solution applied to a column (50 ml bed vol.) of QAE Sephadex ($Cl^-$ cycle) packed in water. The column was eluted with 12% (w/v) NaCl, fractions of 5 ml being collected and assayed by hplc. Fractions 23-30 were combined and desalted on XAD-4 (25 ml). Activity was eluted with 60% aqueous methanol and the active eluates combined, concentrated and freeze-dried to yield 7.2 mg cream coloured solid, containing factor S3907C/3 as the sodium salt; $\lambda$max 288 nm ($E_1^1$ 194 in methanol); $\gamma$1766 ($\beta$-lactam), 1708 ($CO_2R$), 1608 ($CO_2^-$) 1270 $cm^{-1}$ ($OSO_3Na$) and 1240 $cm^{-1}$ ($-OSO_3Na$); n.m.r. consistent with structure.

EXAMPLE 4

Streptomyces sp. S3907C was fermented according to the method of Example 3 except that glucose was also omitted from Medium 3, being added as a continuous feed to give an addition of 0.5% w/v per 24 hours and the pH was not controlled.

The harvest broth (400 liters, pH 7.65) was filtered as in Example 3, the pH of the filtrate (368 liters, pH 8.0) was adjusted to pH 7 with concentrated sulphuric acid (50 ml) and the filtrate was extracted with dichloromethane containing benzyl dimethyl-n-hexadecyl ammonium chloride by the method of Example 3. The extracts were then back extracted into potassium iodide solution and the back extracts treated wit XAD-4 according to the method of Example 3. The eluate fractions which were shown by h.p.l.c. to contain factor S3907C/3 were combined, concentrated and freeze-dried to give 43 g solid.

Solid (19 g) was chromatographed on QAE Sephadex (440 ml) with elution with 10% (w/v) NaCl. Fractions shown by h.p.l.c. to contain largely factor S3907C/3 were combined and desalted to yield a crude solid. The solid was further purified by chromatography on Sephadex LH 20 (1.2 liters) in acetonitrile-water (7:3) followed by concentration and freeze-drying of active fractions to give 226 mg solid. The solid which contained the sodium salt of factor S3907C/3 had the following U.V. spectra:

| $\lambda$max | E: |
|---|---|
| 288 | 230 in neutral methanol |
| 284 | 230 in alkaline methanol |
| 289 | 230 in acidic methanol |

Figure 3:
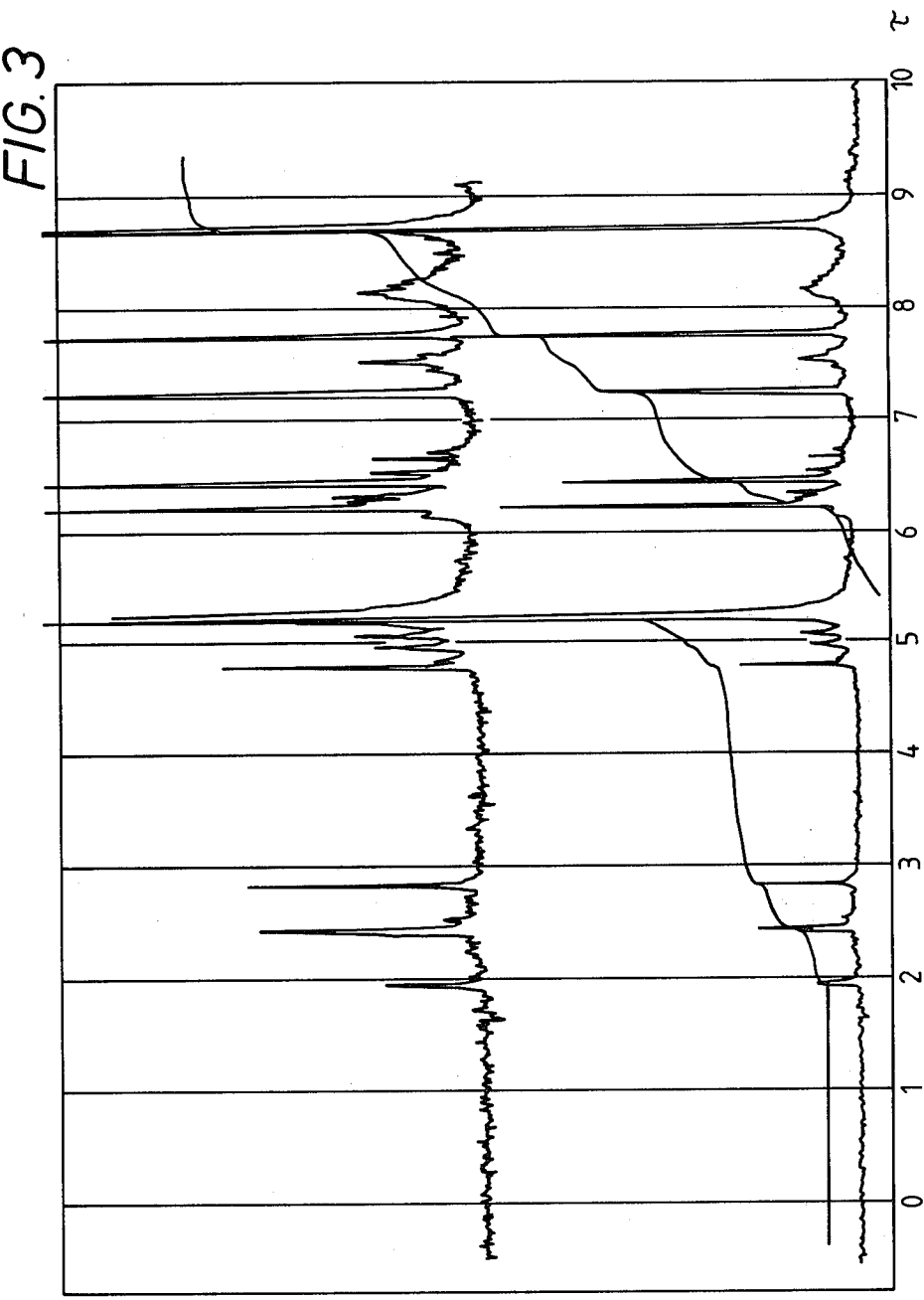
Figure 4:
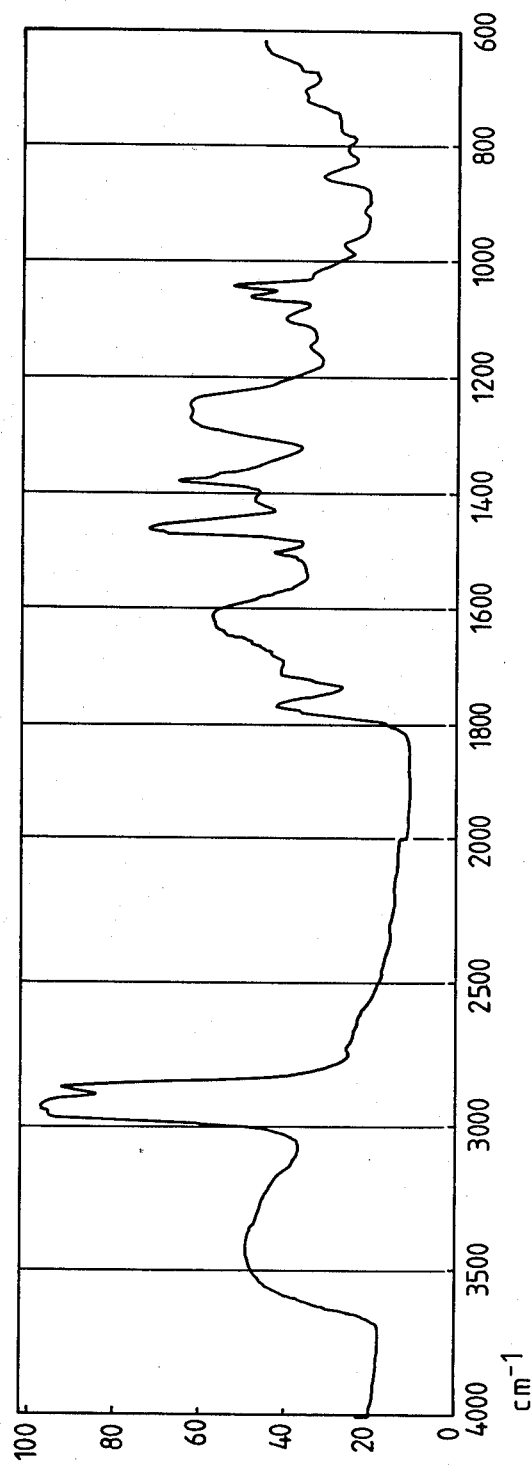

The N.m.r. and I.r. spectra are shown in FIG. 3 and FIG. 4 respectively.

EXAMPLE 5

(a) Streptomyces rochei NRRL 3973 was seeded directly from a freeze-dried ampoule onto an agar slope prepared from Medium 1. A dry scraping from this master slope was then used to inoculate further slopes of Medium 1 which were grown at 28° C. for 14 days.

10 ml of sterile glycerol solution (15% w/v) containing Tween 80 (0.01% w/v) was added to each slope and the spores scraped off the surface with a pipette. From the resulting suspensions, portions (1 ml) were transferred to flasks containing Medium 2 (60 ml). The flasks were incubated for 48 hours at 28° C. on a rotary shaker.

Each flask was then used to provide an inoculation (2 ml) for a flask containing Medium 5 (60 ml). The flasks were incubated for 72 hours at 28° C. on a rotary shaker.

(b) The harvest broth (500 ml) was clarified by centrifugation. The presence of S 3907C/3 was demonstrated by h.p.l.c.

(c) 75 ml of supernatant fluid (pH 7.0) was extracted with $\frac{1}{3}$ volume of dichloromethane (25 ml) containing 0.2% benzyl dimethyl n-hexadecyl ammonium chloride by shaking in a separating funnel and allowing to settle. Activity was back extracted from the dichloromethane extract with 3.5% potassium iodide solution. The presence of 3907C/3 was demonstrated as described above.

EXAMPLE 6

Hydrolysis of S 3907C/3 to 7$\alpha$-methoxy desacetylcephalosporin C catalysed by the esterase from *Rhodosporidium toruloides*

A sample (5.9) mg) of S 3907C/3 ($E_1^1$ at 287 nm=275) was dissolved in water (1.2 ml) containing potassium dihydrogen phosphate (0.16 mmole), and adjusted to pH 6.0. A sample (2 mg) of acetone-dried cells of *Rhodosporidium toluloides* strain CBS 349 (fermented as described in British Patent Specification No. 1,531,212) was then added. After about 21 hours at 28° a portion of the reaction mixture was chromatographed at high pressure (1500 psi) on Partisil 10 SAX (10$\mu$ particle size) using a gradient of potassium dihydrogen phosphate (5 g/liter to 50 g/liter) as the eluant. The reaction mixture was found to contain a uv-absorbing component not present in the original sample. This new component had a column capacity ratio of 3.0 on Partisil 10 SAX. The product of a similar hydrolysis (1 hour at 37°) using 7α-methoxy cephalosporin C (10 mg) as the substrate had the same column capacity ratio on Partisil 10 SAX.

Indication of the relationship between the structures of factors S3907C/3 and S3907C/4B to cephamycins A and B and the antibiotic C-2801-X is provided by the following findings:

1. S3907C/3 is destroyed by the same spectrum of β-lactamases which destroy cephamycins. It also has an antibiotic spectrum similar to that of cephamycin A.

2. Streptomyces Sp. S3907C produces at least one other previously described cephamycin (cephamycin A).

3. The spectroscopic data on S3907C/3 clearly indentifies some features of the cephamycins (for example 7α-methoxy, β-lactam).

4. S3907C/3 is converted into S3907C/4B and in turn to Antibiotic C2801-X by aqueous acidic acetone. This we believe is analogous to the conversion of cephamycin A to cephamycin B in which the aromatic sulphate ester is hydrolysed.

5. P99 β-lactamase releases an acid from S3907C/3 which can also be isolated from the fermentation broth itself. This acid, which contains about two sulphur atoms per ten carbon atoms, is converted by aqueous acidic acetone to m,p-dihydroxy-α-methoxy cinnamic acid via the acid from factor S3907/4B. This acid is esterified to the 3-hydroxymethyl group of antibiotic C-2801-X described in British Patent Specification No. 1,480,082. The following few simple conversions, described in more detail below, have enabled us to confirm the relationship between S3907C/3, S3907C/4B and the antibiotic C-2801-X

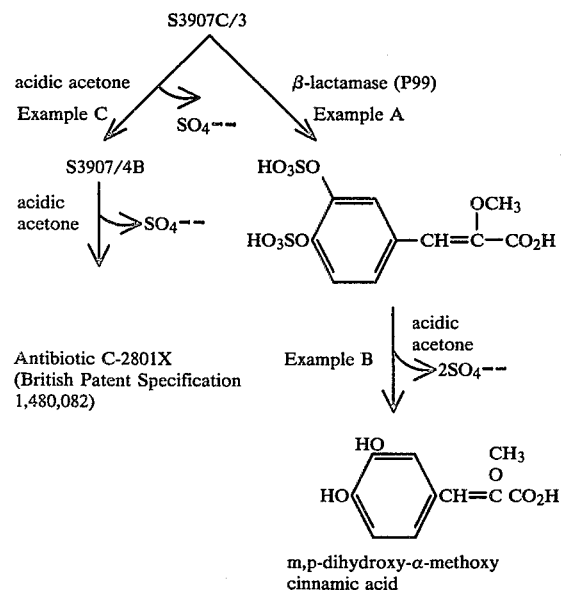

EXAMPLE A

Preparation of the lithium salt of the acid released from S3907C/3 by P99 β-lactamase The concentrated back extract in aqueous potassium iodide solution (5.74 liters) described in Example 2 was passed down a column (1.5 liters) of XAD4. When analysed by h.p.l.c. the column filtrate was found to contain those acids which P99 β-lactamase releases from S3907C/3, cephamycin A and S3907C/4B. After washing the column with water the combined filtrate and water washes (7.0 liters) was run onto a column of Pittsburgh CAL charcoal (500 ml). The column was washed with water (500 ml) and eluted with 50% aqueous methanol, collecting fractions of 250 ml. Fractions were examined by h.p.l.c. and those rich in "S3907C/3 side-chain acid" (1–4) were combined, concentrated and freeze-dried to give 6.8 g solid.

Solid (6.0 g) was dissolved in 30 ml water and this solution applied to a column (3.5×48 cm; 450 ml bed vol.) of QAE Sephadex (Cl⁻ cycle) equilibrated with water. The column was eluted with a 0–10% linear gradient of lithium chloride (2.0 liters) followed by 10% lithium chloride at 75 ml/h. Fractions of 25 ml were collected and assayed by hplc. Fractions 102–135 were combined and passed through a column of Pittsburgh CAL charcoal (100 ml) at 400 ml/h. The column was washed with water (100 ml) at 400 ml/h. The column was washed with water (100 ml) and eluted with 50% aqueous methanol, taking fractions of 100 ml. Fractions 1–3 were combined and concentrated by rotary evaporation. The concentrate was adjusted to pH 7 with dil. HCl and freeze-dried to yield 785 mg solid (Solid 1).

The water wash from the charcoal column, shown by hplc to contain a considerable amount of the required compound, was passed down a column (50 ml) of Ambersorb XE-348. The column was washed with water (50 ml) and eluted with 50% methanol. Concentration and freeze-drying of this eluate yielded a further 187 mg solid (Solid 2).

Properties of "S3907C/3 side-chain acid" (Lithium salt)

Figure 5:
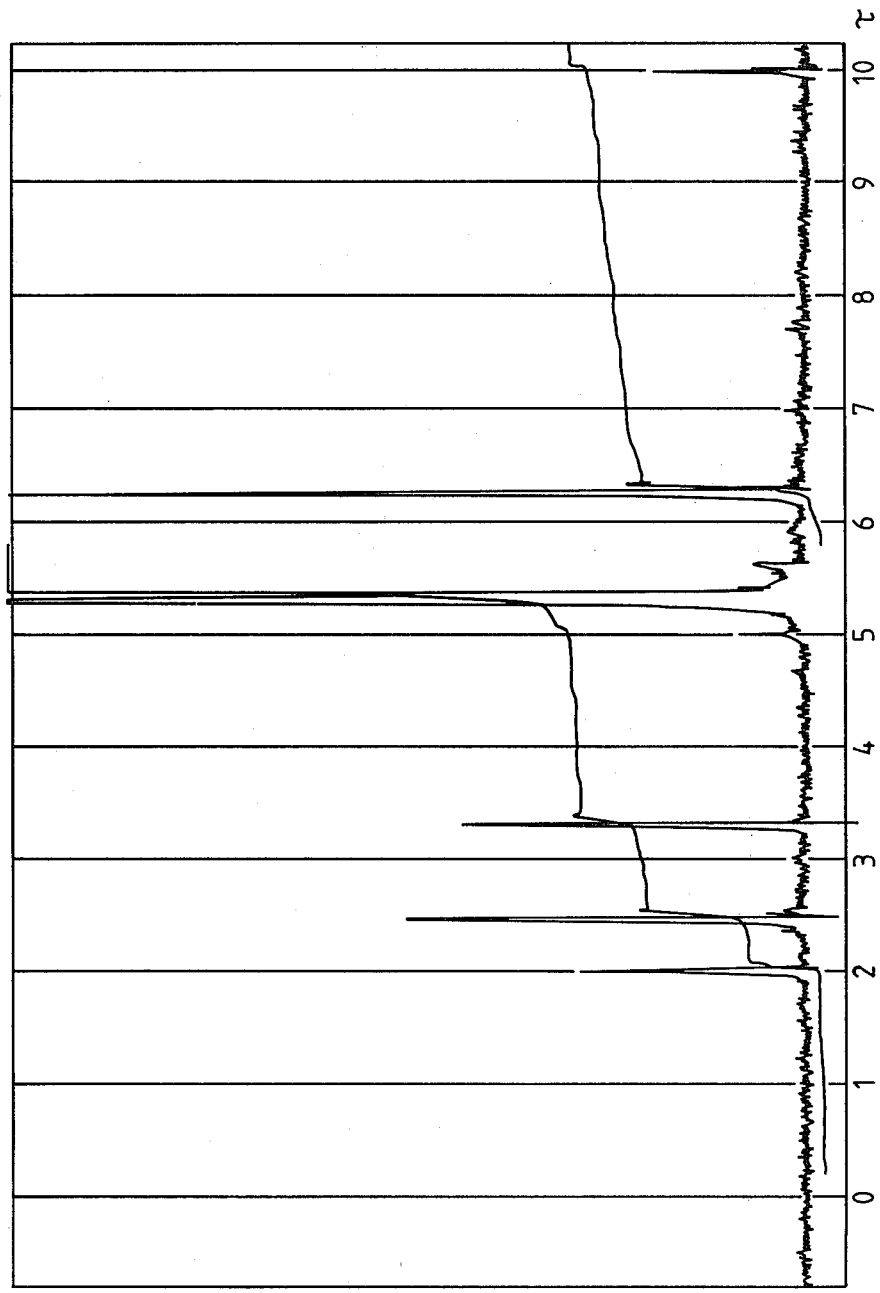
Figure 6:
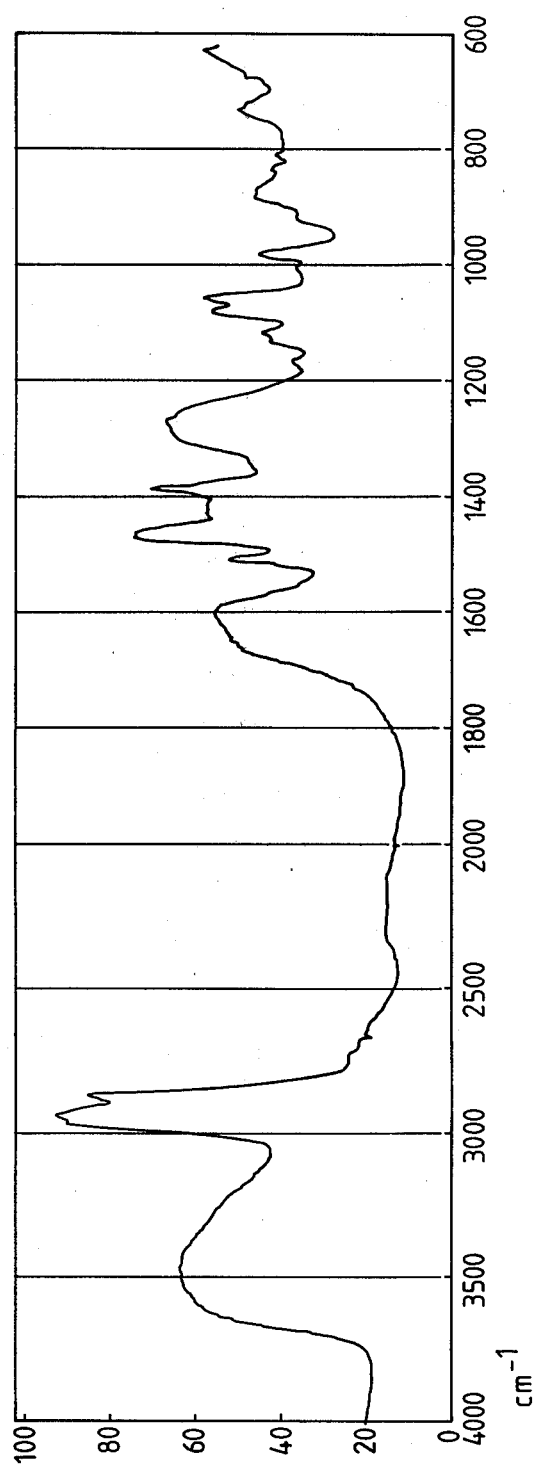

N.m.r. and I.r. spectra of the side-chain acid are shown in FIG. 5 and FIG. 6 respectively.

| | | Solid 1 | | |
|---|---|---|---|---|
| U.V. | λmax | E: | Solvent | λmin |
| | 280 | 460 | water/alkali | 239 |
| | 287 | | acid | 244 |

| | | Solid 2 | | |
|---|---|---|---|---|
| N.m.r. | Consistent with structure. No impurity except H₂O | | | |
| I.r. | 1600 cm⁻¹ (CO₂R) and 1268 cm⁻¹ (—OSO₃Li) | | | |
| U.v. | $\lambda_{max}$ | E: | Solvent | $\lambda_{min}$ |
| | 280 | 530 | H₂O or dilute alkali | 239 |
| | 287 | 520 | dilute acid | 243 |

EXAMPLE B

Preparation of m,p-dihydroxy-α-methoxy cinnamic acid

Solid 1 (785 mg) described in Example A, was dissolved in 250 ml 95% aqueous acetone. A few drops of conc. HCl were added and the mixture stood at room temperature. After 18 h, examination by h.p.l.c. showed all the starting material to have been consumed. A mixture of products was present. One component had an identical column capacity ratio (11.4) to the acid released from S3907C/4B by P99-β-lactamase and a second component had a column capacity ratio of 1.8.

After a further 70 h conversion was shown by h.p.l.c. to be complete and only the product of column capacity ratio 1.8 was present. To the solution was added 30 ml water, then the acetone was removed by rotary evaporation to leave an aqueous solution (45 ml) at pH 1.4. This was extracted with 50 ml ethyl acetate and the organic layer separated and evaporated to give a yellow solid. The solid was recrystallised from water (35 ml) to give white crystals, which were filtered and dried under vacuum to give 190 mg. On standing, the mother liquors produced a second crop which was filtered and dried to give 17 mg.

Properties of m,p-dihydroxy-α-methoxycinnamic acid Mass spectrum F.D. spectrum showed a parent ion at m/e 210

This supports the molecular formula $C_{10}H_{10}O_5$

N.m.r.

![structure: dihydroxy benzene ring with CH=C(CO2H)(OCH3) substituent, protons labeled a, b, c, d, e]

| Proton | Chemical shift (τ) | Literature Chem. Shift (τ) |
|---|---|---|
| a | 2.59 | 2.65 |
| b | 3.23 | 3.25 |
| c | 2.95 | 2.97 |
| d | 3.08 | 3.10 |
| e | 6.29 | 6.30 |

I.r. The I.R. spectrum was similar to that shown in FIG. 2 of the reference below.
Absorptions at 3500, 1195 (—OH) 1640, 1665 (α,β-unsaturated carboxylic acid) and 1610, 1520 and 905 cm$^{-1}$ (aromatic ring) as described in the original report of this material.

U.v. λmax E:

| 220 (218) | 580 | } in neutral methanol |
| 294 (294) | 690 | |
| 318 (318) | 680 | |
| 250sh (250sh) | 410 | } in alkaline methanol |
| 304 (300) | 525 | |
| 335 (335) | 710 | |

Values in brackets are from Structure of C-2801X, a Cephamycin-type antibiotic. Fukase, H. & Iwasaki, H., Bull. Chem. Soc. Japan (1976), 49, 767–70.

Microanalysis
Found: C, 54.4; H, 4.9; S, Nil Calcd: C, 57.14; H, 4.80; S, Nil.

EXAMPLE C

Hydrolysis of S3907C/3 by acidic acetone

When a small sample of the solid from Example 4 was treated with a mixture (9:1 v/v) of acetone and 0.1 M-HCl, the S3907C/3 it contained was rapidly degraded. When analysed by h.p.l.c. after a few minutes at room temperature the solution was found to contain S3907C/3 column capacity ratio 14.6 and the acid released from S3907C/3 by P99 β-lactamase (column capacity ratio 20.2). The solution also contained S3907C/4B (column capacity ratio 8.6) and the acid (column capacity ratio 11.4) released from S3907C/4B by P99 β-lactamase. Products absorbing at 280 nm also included one with a column capacity ratio 1.8 similar to that of the acid identified in Example B.

EXAMPLE D

Hydrolysis of S3907C/3 by P99 β-lactamase

About 10 μg S3907C/3 was hydrolysed in 50 μl water at room temperature. The water also contained 0.31 mg ammonium acetate (pH about 7.5), 2.3 mg sodium chloride and 0.06 units P99 β-lactamase (one unit hydrolyses 1μ mole cephaloridine per min at 37°). A control hydrolysis was also prepared from which the P99 β-lactamase had been omitted.

After 15 min a sample (5 μl) of each hydrolysis was separated by h.p.l.c. The major peak in the sample from the control hydrolysis had a column capacity ratio of 13.1 (S3907C/3). This peak was absent from the sample incubated with the P99 β-lactamase and was replaced by a peak with a column capacity ratio of 21.8 (side chain from S3907C/3).

We claim:

1. A compound of the formula (I)

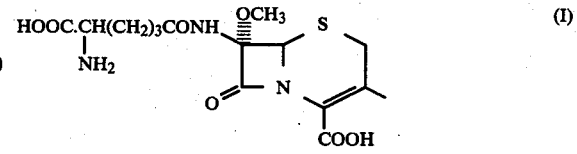

wherein R$^1$ represents a hydroxyl or sulphooxy group R$^2$ represents a sulphooxy group, or a salt, ester, N-protected derivative or solvate thereof.

2. An alkali metal, alkaline earth metal, ammonium or organic base salt of claim 1.

3. A lithium or sodium salt which is a compound as claimed in claim 1.

* * * * *